United States Patent [19]

Gaccione

[11] 4,106,199

[45] Aug. 15, 1978

[54] AMALGAMATOR

[76] Inventor: Carmine Gaccione, John Jay Pl., Rye, N.Y. 10580

[21] Appl. No.: 748,065

[22] Filed: Dec. 6, 1976

[51] Int. Cl.² .............................................. A61C 5/06
[52] U.S. Cl. ..................................... 32/40 A; 32/51; 32/60
[58] Field of Search ..................... 32/60, 40 A, 51–55, 32/27

[56] References Cited

U.S. PATENT DOCUMENTS 1,694,857  12/1928  Kulik ......................................... 32/60
3,611,573  10/1971  Crawford et al. .................. 32/40 A

*Primary Examiner*—Robert Peshock

[57] ABSTRACT

A dental tool for measuring, triturating and dispensing amalgam having a hand piece holding a reciprocable chamber into which the amalgam ingredients are metered and then shaken is provided with an opening through which the triturated amalgam can be dispensed into a cavity. A pin mounted in the receptacle can be used to valve the passageway out of the receptacle and functions also as a tamper when the receptacle is reciprocated for tamping dispensed amalgam into a cavity.

3 Claims, 4 Drawing Figures

AMALGAMATOR

This invention relates to the preparation and dispensing of amalgams of silver and mercury utilized in dentistry for filling cavities in teeth and in particular provides the hand-held tool suitable for triturating, dispensing and tamping amalgams. In filling cavities in teeth and particularly, small cavities, the use of silver amalgam has long been in practice. The silver amalgam is prepared generally utilizing an 8:5 mixture by weight of mercury and silver alloy and traditionally has been prepared by the time-consuming process of weighting and mixing (triturating) to proper consistency utilizing a mortar and pestle. More recently, mechanical devices have been devised for triturating but the need of handling the amalgam by the use of carriers and vibrators has remained.

It is thus a principal object of the present invention to provide a dental tool of the hand-held type which can suitably be driven by a dental machine which will accomplish the steps of triturating the amalgam, dispensing the amalgam and tamping it in the cavity. In a more sophisticated aspect of this invention is also an object to provide such a hand-held tool which not only will triturate, dispense and tamp, but which can also be connected to separate sources of silver alloy and mercury and meter these into the triturating device in proper proportion.

These and other objects of the invention are essentially obtained utilizing a hand piece in the form of a housing member, preferably elongated and with an offset such as is used in an ordinary dental tool of the machine driven type, which is provided with a transverse bore suitably formed by a sleeve on the end of the tool. The bore contains an amalgamator receptacle which is mounted so that it can be reciprocated rapidly to accomplish trituration of mercury and silver alloy placed in the receptacle. The receptacle at one end is provided with a restricted passageway which communicates with its interior to permit ejection of contents from the receptacle. Ejection of the amalgam is accomplished by the use of a valve pin which extends through the passageway in one position and which can be withdrawn in a second position into the chamber to open the passageway. When the valve pin is then moved to close the passageway again, the contents of the receptacle are forced out through the passageway, e.g. into the cavity. The valve pin extends slightly out of the receptacle in the first position so that it can operate as a tamping tool, with tamping aided by the limited reciprocation of the receptacle in which the valve pin is mounted.

In a preferred embodiment, the tool is also provided with connections to a supply of silver alloy and a supply of mercury and has a metering arrangement in which compressed air is utilized to cause the mercury and alloy flow through separate passageways and a valve arrangement permitting volumetric measurement of the precisely required quantities of alloy and mercury and their delivery to the receptacle.

For a more complete understanding of the practical application of this invention, reference is made to the appended drawings in which.

Figure 1:
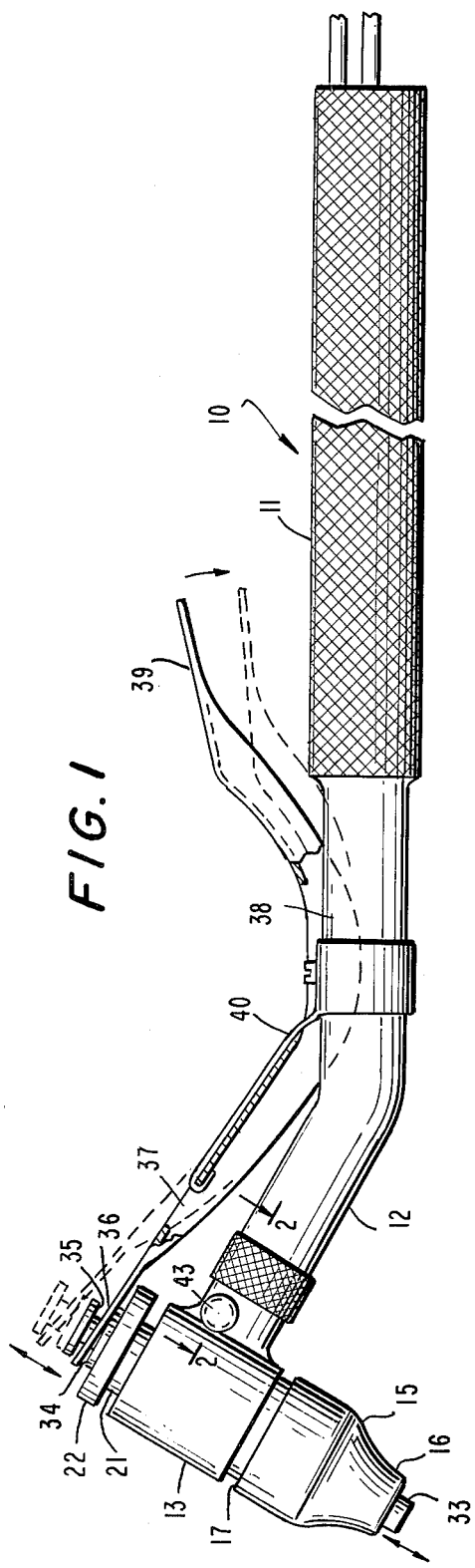
FIG. 1 is an elevation of a dental tool in accordance with the present invention.

In the drawings the reference numeral 10 generally designates a dental tool in accordance with the present invention for metering, triturating, dispensing and tamping amalgam. Amalgamator 10 includes a generally cylindrical elongated handle 11 having an end 12 offset at a slight angle, as is conventional with contra angle hand pieces in order to facilitate bringing a contra angled head into contact with the occlusal surfaces of the teeth. Handle 11 at end 12 terminates in a transverse sleeve 13 generally at right angles to the lengthwise axis of end portion 12.

The bore 14 of sleeve 13 thus opens at each end and receives amalgamator receptacle 15 which is generally cylindrical, and sized to be slidably but securely fitted in bore 14. Receptacle 15 has one end portion 16 closed with a lip or flange 17 which projects outwardly such that it acts as a stop on movement of receptacle 15 through sleeve 13. End 16 is on the underside of hand piece 10, faces the original line of handle 11 before offset end 12 and is the discharge end of the chamber 18 formed within receptacle 15. End 16 is further provided with a short axial passageway 19 of restricted cross dimension which functions, as will be later described, as a dispensing exit from chamber 18. The other end 20 of receptacle 15 is tapped and provided with an end cap 21 which is threadedly received in end 20 to close end 20. Cap 21 is provided moreover with a flange 22 which extends outwardly of the outer walls of receptacle 15 and thus functions as a stop limiting travel of receptacle 15 in sleeve 13 opposing the stopping action of lip 17. Cap 22 is further provided with an axial bore 23 which is aligned with passageway 19 in end 16 of receptacle 15.

A drive shaft 25 extends lengthwise through handle 11 with suitable bevel gear connections to accommodate offset 12 and is provided at its end remote from sleeve 13 with a connection to a dental machine by pulleys and the like or, in the preferred arrangement, with a high speed air-driven turbine capable of rotating shaft 25 at speeds of 15,000 rpm. Shaft 25 at its ended adjacent sleeve 13 passes through a bearing 27 and terminates internally within bore 14 of sleeve 13 within an eccentric cam 28. The exterior of receptacle 15 at the location of cam 28 is recessed at 29 to receive cam 28 permitting rotation of cam 28 in recess 29 such that as shaft 25 is rotated, cam 28 moves eccentrically in recess 29 causing receptacle 15 to reciprocate in bore 14. The amount of reciprocation required is not critical and typically is on the order of one millimeter when the rotational speed of shaft 25 is on the order of 15,000 rpm.

Receptacle 15 is provided with a valving device which functions as a condenser plugger and tamping mechanism and is in the form of a pin 31 which has a central cylindrical body portion 32 extending in length from the bottom inside of chamber 18 through bore 23. At its end 33 adjacent receptacle end 16 pin 31 has a reduced diameter sized to fit slidingly and sealingly through passageway 19 and is of sufficient length to extend a short distance beyond end 16 of receptacle 15. At its other end exteriorly of cap 21 pin 31 is provided with a pair of confronting shoulders 34 and 35. These receive a loop 36 on the end of an actuating lever 37 which is pivotally seated on handle 11 at 38. The end 39 of lever 37 remote from loop 36 is biased by spring 40 away from handle 11 such that loop 36 normally bears against shoulder 34 tend to hold pin 31 in position in which end 33 extends through passageway 19 sealing such passageway. When lever end 39 is depressed toward handle 11, sliding movement of loop 36 against shoulder 35 lifts pin 31 withdrawing end 33 into chamber 18 and opening communication through passageway 19 into chamber 18.

Figure 3:
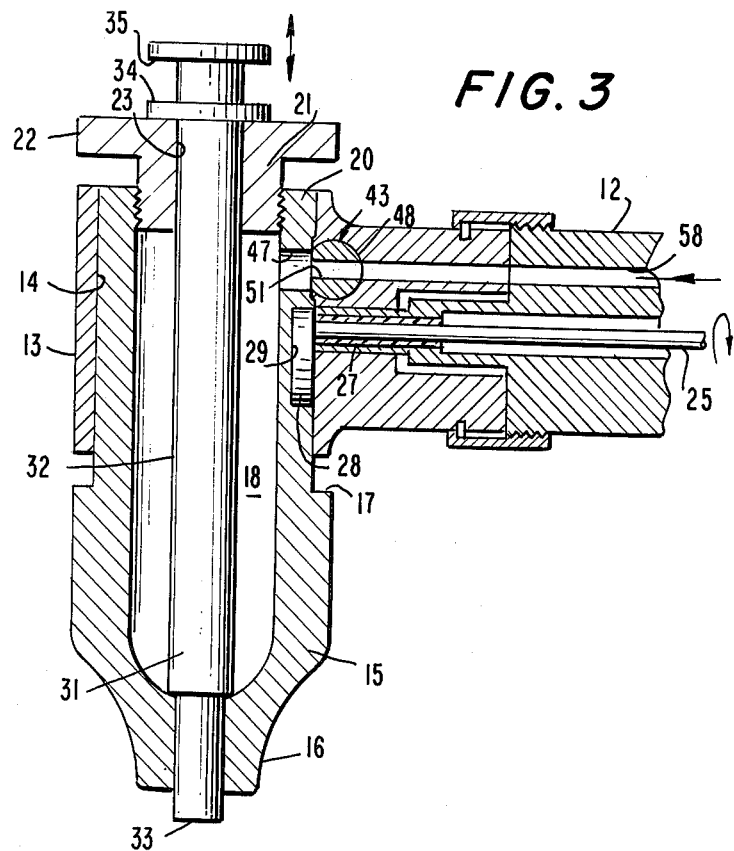
FIG. 3 is an enlarged sectional view of the triturating head and dispensing mechanism taken at line 3 — 3 in FIG. 2.
Figure 4:
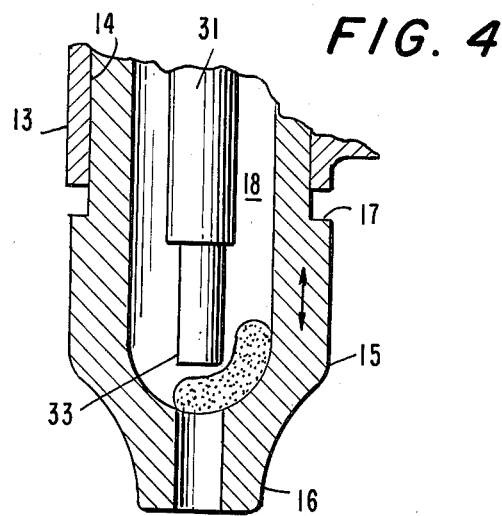
FIG. 4 is a view similar to FIG. 3 showing the triturating head in an intermediate position in dispensing the amalgam.

In employment, chamber 18 is filled with the proper metered charges of silver alloy and mercury, for example by opening cap 21 and introducing them. Thereafter cap 21 is closed, and shaft 25 is rotated and thus reciprocates receptacle 15 at a rapid rate through a limited distance determined by the eccentricity of cam 28. This action produces trituration of the silver alloy and mercury and formation of the amalgam. With shaft 25 then deactivated, manipulation of handle 39 of lever 37 permits the charge of amalgam to be rotated to a position over passageway 19 as shown in FIG. 3. Handle 39 is then released to cause the charge to be pushed into passageway 19. Several movements of lever 37 may be required in order to place all of the amalgam charge in passageway 19. Tool 10 is then put in position with pin 31 raised to discharge the contents of passageway 19 into the cavity to be filled by releasing lever 37 under its spring compressing to force the amalgam into the tooth with the end 33 of pin 31 acting as a tamp. Finger pressure on pin 31 can also be used to express the charge of amalgam in passageway 19 into a cavity. Tamping can be aided by reactivating rotation of shaft 25 such that a vibratory motion is imparted to end 33 of pin 31.

Rather than separately metering the silver alloy and mercury to charging chamber 18 of receptacle 15 through 20, dental tool 10 is preferably provided with a mechanism by which connection to a supply of silver alloy and a supply of mercury can be made with metering built in to handle 11 utilizing compressed air to feed the powdered silver alloy and liquid mercury through tubes in handle 11.

In order to accomplish this connections 41 and 42 are provided in handle 11 which leads through metering device 43 in offset end 12 to a pair of horizontally separated ports 46 and 47 in the wall of receptacle 15. Connection 41 functions as an alloy duct for delivering silver alloy into chamber 18, and connection 42 functions as a mercury duct for delivering mercury into chamber 18. Tubes 41 and 42 lead back through handle 11 to supply lines for feeding powdered silver and liquid mercury respectively to tubes 41 and 42. While air pressure on the mercury supply is adequate to force mercury through connection 42, alloy duct 41 can also include a positive feed device, such as a screw conveyer.

Figure 2:
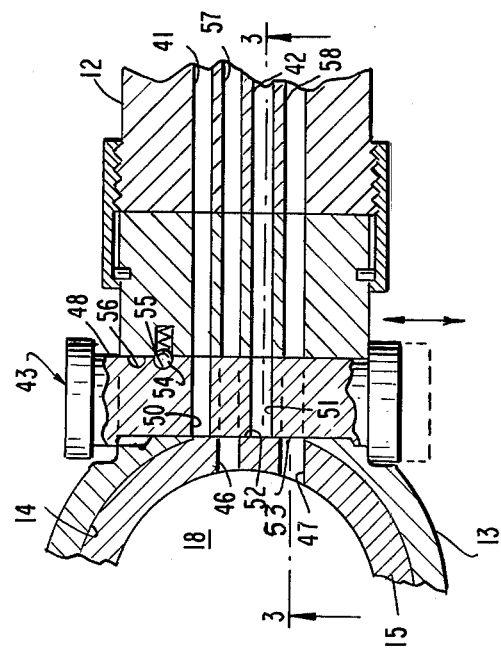
FIG. 2 is a schematic, enlarged section of the metering mechanism utilized in the tool shown in FIG. 1 taken at line 2 — 2.

The functioning of metering device 43 is more clearly shown with reference to FIG. 2 and 3. Metering device 43 is in the form of a cylindrical plunger 48 mounted horizontally in handle end 12 transverse to and above the center line of end 12 to clear passage of shaft 25. Plunger 48 has its ends extending out of handle end 12 on each side and contains two bores through it indicated by the reference numerals 50 and 51. Plunger 48 is adjacent sleeve 13 and has a portion extending through sleeve 13 in sliding contact with the outer wall pf receptacle 15. Vertical movement of receptacle 15 and horizontal movement of plunger 48 in continued sliding contact are accommodated by flatting their contacting surfaces, as indicated at 52 and 53.

Ports 46 and 47 are located in flat 52 and are vertically elongated to facilitate registration with bores 50 and 51 in the discharge position of plunger 48 described below. Bores 50 and 51 at one pair of ends thus are located in flat 53.

Plunger 48, as suggested above, is horizontally slidable in end 12 between a "charge" position and a "discharge" position. A spring loaded ball 54 in handle 11 and a pair of depressions 55 and 56 in plunger 48 are arranged such ball 54 seats in depression 55 in the "charge" position and in depression 56 in the "discharge" position of plunger 48. In the "charge" position of plunger 48 the ends of bores 50 and 51 in flat 53 are sealed against flat 52, as shown in solid lines in FIG. 2. The other ends of bores 50 and 51 register with the ends of connections 41 and 42 and fill with alloy and mercury, respectively. The volumes of bores 50 and 51 in plunger 48 are sized such that when filled with silver alloy powder and liquid mercury, these components are in the proper ratio (8:5 by weight) for metering a charge of ingredients to mix amalgam. In the discharge position (dashed line) of plunger 48 the ends of bores 50 and 51 in flat 53 are lined up respectively with ports 46 and 47 in receptacle 15. The other ends of bores 50 and 51 are lined up with compressed air connections 57 and 58 in end 12 of handle 11, such that compressed air blows the charges in bores 50 and 51 through ports 46 and 47 respectively into chamber 18 loading it with the proper ingredients for preparing a charge of amalgam.

The operation device is then as described above.

I claim:

1. A dental amalgam triturating and dispensing tool which comprises:

a housing member including means defining a bore extending transversely through said member and having an opening therefrom on one side of said member, an amalgamator receptacle defining a closed chamber, said receptacle being slidably positioned in said bore and adapted for reciprocating movement therein with an end portion of said receptacle exposed through said opening of said bore, and a restricted passageway communicating with said chamber interior extending through said end portion of said receptacle, valve means including a pin having a tamping-head portion at one end thereof, said pin being mounted in said chamber for reciprocating movement between a first position with said tamping-head portion extending outwardly of said chamber through said passageway thereby sealing said passageway and projecting therebeyond and a second position with said tamping-head portion withdrawn into said chamber, thereby permitting communication between said chamber and the exterior of said receptacle through said passageway, drive means in said member for reciprocating said amalgamator receptacle through a limited distance in said bore, and means for moving said pin between said first and second positions thereof, said drive means including a cam, rotatable shaft means in said member for rotating said cam, and a recess in the exterior of said receptacle, said cam being positioned adjacent the wall of said bore engaging said recess.

2. A dental tool according to claim 1 in which said housing member is an elongated hand-piece and said included in said housing member defining a bore is a sleeve mounted on an end of said member.

3. A dental tool according to claim 1 which further comprises feed means for measuring and introducing metered quantities of mercury into said receptacle and feed means for measuring and introducing metered quantities of silver alloy into said receptacle.

* * * * *